(12) United States Patent  
Sihalla

(10) Patent No.: US 7,437,248 B2  
(45) Date of Patent: Oct. 14, 2008

(54) WATER QUALITY SAMPLING SYSTEM

(76) Inventor: Zakaria Sihalla, 324 Axis Deer Trail, Hutto, TX (US) 78634

( * ) Notice: Subject to any disclaimer, the term of this patent is extended or adjusted under 35 U.S.C. 154(b) by 175 days.

(21) Appl. No.: 11/480,790

(22) Filed: Jul. 3, 2006

(65) Prior Publication Data

US 2008/0011061 A1   Jan. 17, 2008

(51) Int. Cl.  
*G01N 31/00*   (2006.01)  
*G06F 19/00*   (2006.01)

(52) U.S. Cl. ......................................... 702/22

(58) Field of Classification Search ............... 702/22  
See application file for complete search history.

(56) References Cited

U.S. PATENT DOCUMENTS

| | | | |
|---|---|---|---|
| 3,913,384 A * | 10/1975 | Furuya et al. | 73/53.01 |
| 4,367,652 A * | 1/1983 | Venuso | 73/861 |
| 4,434,364 A * | 2/1984 | Correa et al. | 250/253 |
| 4,499,762 A * | 2/1985 | Bodge et al. | 73/170.01 |
| 4,763,537 A * | 8/1988 | Scott et al. | 73/170.29 |
| 4,908,105 A | 3/1990 | Garnet, Jr. | 201/1 |
| 5,302,347 A * | 4/1994 | Van Den Berg et al. | 422/67 |
| 5,401,412 A * | 3/1995 | Yang et al. | 210/605 |
| 5,821,405 A | 10/1998 | Dickey | 73/53.01 |
| 6,111,249 A | 8/2000 | Garner, III | 250/239 |
| 6,197,256 B1 * | 3/2001 | Siepmann | 422/79 |
| 7,103,481 B2 * | 9/2006 | Negri | 702/22 |
| 2005/0121536 A1 * | 6/2005 | Bavel | 239/69 |

FOREIGN PATENT DOCUMENTS

JP      2005-193236      *   7/2005

* cited by examiner

*Primary Examiner*—Michael P. Nghiem  
*Assistant Examiner*—Cindy H Khuu  
(74) *Attorney, Agent, or Firm*—Robert V. Wilder

(57) ABSTRACT

A method and system are provided in which a water sensing device is equipped with a water-sealed sampling chamber enclosing the sensing probes of the sensing device. When the device is placed into its water habitat, water flow into and out of the sampling chamber is controlled such that water is present in the sampling chamber only during a relatively brief period of time when water quality measurements are taken by the probes. After the water quality measurements have been taken by the probes, the water sample is substantially pumped out of the sampling chamber so as to minimize the time during which the probes are in contact with the water being analyzed.

20 Claims, 5 Drawing Sheets

WATER QUALITY SAMPLING SYSTEM

FIELD OF THE INVENTION

The present invention relates generally to water quality sampling systems and more particularly to a system and apparatus for enabling long term deployment of water quality sensor devices.

BACKGROUND OF THE INVENTION

For many reasons, water quality, and the monitoring and testing of water, has become a very important undertaking in today's environment. More and more bodies of water are being monitored for quality on a regular basis. Further, water samples are being taken, analyzed and recorded for a greater number of locations within given bodies of water.

The water samples are taken and analyzed in order to determine resident amounts of various chemicals and biological elements. These measurements are then logged into a database for subsequent planning purposes. As various actions are taken to purify or de-contaminate the water, sampling-is again used to determine whether or not the water treatment plans are effective.

Currently, all government and state agencies are monitoring water quality using multi-sensor units called "multi-probes".

The sensing devices or multiprobes are equipped with sensors to measure different water quality parameters or characteristics such as, inter alia, pH, dissolved oxygen, conductivity, salinity, temperature, turbidity, ammonia, nitrate, Oxidation Reduction Potential (ORP), and many others. The sensor devices also include an electronic circuit board in a water-sealed housing as well as a real time electric clock, analog and digital circuitry to control the operation of the sensors based upon a real time schedule. The multiprobes or sensor units are continuously submerged in water during the deployment time. Sediments and biological life in the water cause fouling of the sensors or probes and affect the sensor's performance and longevity.

In a typical application, a water sensing device is placed under water at a location where the water is to be analyzed. Periodically, according to a programmed schedule, different measurements are taken by various sensors or probes which are mounted at the end of the water sensing device within the water. These readings are stored in memory onboard the sensing device and periodically the sensing device is pulled from the water and connected to a computer, for example a personal computer (PC) or laptop computer, where the readings that had been taken are transferred from the sensing device to files on the PC for further processing, recording and distribution.

As hereinbefore noted, a main problem for this method of water testing is the fouling process which occurs because the water to be analyzed is in constant contact with the testing probes. As a result, sediments, biological life and other factors take their toll of the sensing probes and, over time, render the probes inaccurate if not ineffective. If the fouling problem is not corrected by cleaning the probes on a regular basis, the readings taken by the sensing device are inaccurate and sometimes readings cannot even be taken rendering the water sensing device useless.

In the past, this problem has been corrected by physically removing the sensing device from its water habitat, and physically cleaning the sensors or sensing probes before re-installing the sensing devices to their testing locations under water. However, this process is quite expensive and requires much manpower to keep the sensing probes clean so that accurate readings can be taken and the readings can be relied upon in making water treatment plans.

Thus, there is a need for an improved processing system and apparatus which enables a longer term deployment of water quality sensing devices and less frequent cleaning time for such devices.

SUMMARY OF THE INVENTION

A method and system are provided in which a water sensing device is equipped with a water-sealed sampling chamber enclosing the sensing probes of the sensing device. When the device is placed into its water habitat, water flow into and out of the sampling chamber is controlled such that water is present in the sampling chamber only during a relatively brief period of time when water quality measurements are taken by the probes. After the water quality measurements have been taken by the probes, the water sample is substantially pumped out of the sampling chamber so as to minimize the time during which the probes are in contact with the water being analyzed.

BRIEF DESCRIPTION OF THE DRAWINGS

A better understanding of the present invention can be obtained when the following detailed description of a preferred embodiment is considered in conjunction with the following drawings, in which.

DETAILED DESCRIPTION

Figure 1:
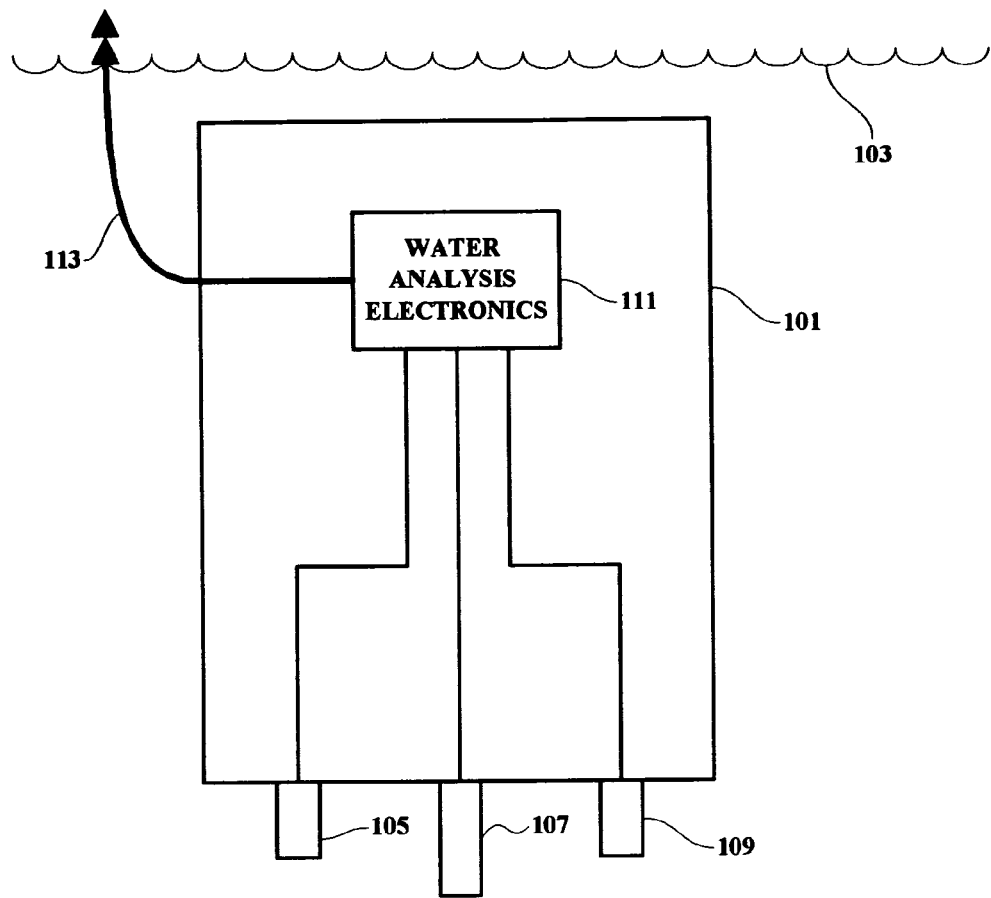
FIG. 1 is an illustration of a prior art water sensing device.

It is noted that circuits and devices which are shown in block form in the drawings are generally known to those skilled in the art, and are not specified to any greater extent than that considered necessary as illustrated, for the understanding and appreciation of the underlying concepts of the present invention and in order not to obfuscate or distract from the teachings of the present invention.

With reference to FIG. 1, there is shown a prior art water sensing device 101 positioned in a normal deployment mode below the surface 103 of a body of water at a point where the water is to be measured and analyzed. The sensing device 101 includes sensing probes 105, 107 and 109 for sensing various characteristics of the water surrounding the probes. In the example, only three probes are shown for simplicity although the exact number of probes for any application will vary depending upon the characteristics of the water which are being sensed. When the sensing device 101 is deployed under water as shown, the probes 105, 107 and 109 are in constant contact with the surrounding water. The probes 105, 107 and 109 are connected to a circuit board 111 which contains water analysis electronics. The sensing device 101 also includes connection means 113 for electrically connecting the sensing device 101 to a computer system such as a laptop or personal computer (PC), both while the sensing device 101 is in the water and also when the device is removed from the water for cleaning and/or maintenance.

Figure 2:
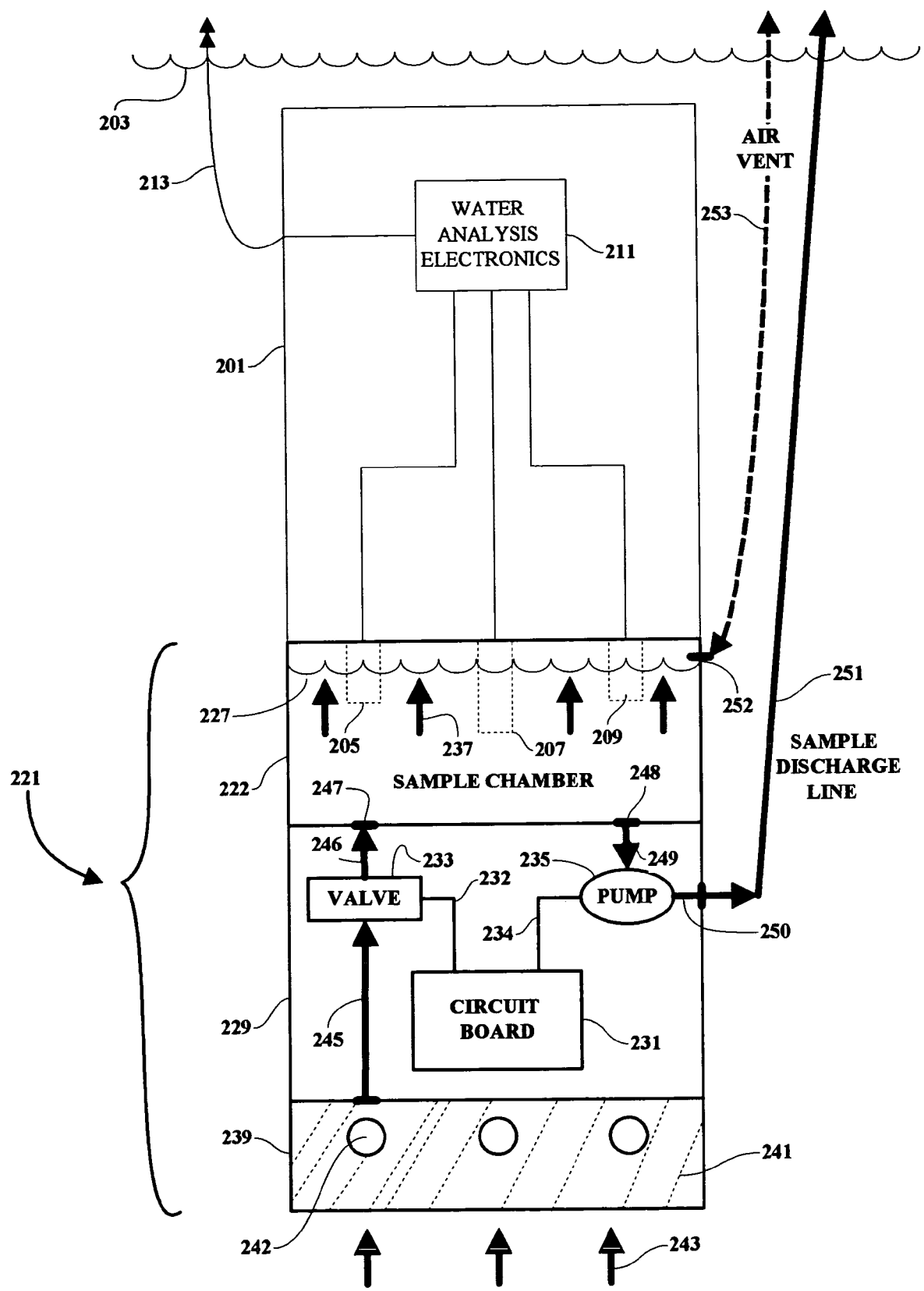
FIG. 2 is an illustration of a water sensing device including an exemplary implementation of the present invention.

FIG. 2 illustrates a sensing device 201, circuit board 211, probes 205, 207 and 209 and connecting electrical cable 213. The device 201 is shown deployed below water level 203. The device 201 also includes a water sampling module 221 in accordance with the present invention. It is noted that there are several functions of the water sampling operation of the present invention which may be synergistically shared with the water sensing device 201, and the present invention may be implemented in either form, either as an attachable portion or module to the sensing device 201, or as an integral part of a water sensing device 201. When the module is manufactured as an integral part of the water sensing device 201, the device clock may be used as a system clock and a synchronization function within the sampling module will not be needed. Further, the circuit board described herein as part of the sampling module 221 may be directly implemented into the circuit board of the sensing device 201 and, in that case, the valve, hold and pump-out functions of the sampling module can be directly controlled from the module control circuitry, whether it is integrated into the sensing device board 211 or as a stand-alone board 231 as shown in the present example.

The sampling module 221 in the present example contains several sections. A sample or sampling chamber 222 is shown connected to the lower portion of the sensing device 201 and placed so as to enclose the probes 205, 207 and 209 of the device 201 within the sampling chamber 222. The sampling chamber is totally water-sealed from the surrounding water and from the water sensing device 201 and the lower sections of the module 221, except for a water inlet 247 for allowing water to flow into the chamber 222, and a water outlet 248 for allowing water to be evacuated from the chamber 222 at the proper times as is hereinafter explained in greater detail. The sampling chamber 222 also has an air vent 252 which is allowed to vent to outside air through air vent tube 253. Outside air moves through the air vent into the chamber when water is being pumped out of the chamber 222, and air is forced through the air vent 252 to outside air supply as water is allowed to fill the sampling chamber 222. A second or component section 229 of the sampling module 221 contains a valve device 233, a pump 235 and a circuit board 231. The second section is also water sealed from the surrounding water. A third section 239 of the sampling module 221 is open to surrounding water at the bottom and through holes 242. The third section 239 acts as an interface to the surrounding water to selectively allow water to enter the sampling module through the filter material 241.

In operation, at a designated time prior to a time when the probes 205, 207 and 209 are powered-up take readings, valve 233 is opened and water surrounding the lower portion of the module 221 enters the module through the bottom section as shown 243 and it is filtered by filter material 241 before passing through a conduit 245 and the valve 233 to the sampling chamber 222. When the valve 233 is opened, the water to be sampled is allowed, through hydrostatic pressure, to pass through conduit 246, enter and eventually fill-up 237 the sampling chamber 222 as indicated 227 in the drawing, surrounding the probes 205-209. In the present example, the valve is opened for a predetermined first time period sufficient to allow the sampling chamber 222 to fill. After the first time period, the valve is closed and measurements are then taken by the probes 205-209. The valve 233 remains closed for a second time period to allow sufficient time for the probes 205-209 to take measurements of the water in the sampling chamber 222. After the second time period has expired, the pump 235 is turned ON for a predetermined third period of time, i.e. a pump ON time, and the sampled water is pumped through outlet 248, conduit 249, pump 235 and conduit 250 to a discharge line 251 and then to the outside water surface 203. In the present example, the sampled water is discharged to the water surface away from the water inlet area 243 so as not to disturb the water surrounding the inlet area 243 and also to prevent re-reading the same water samples. After the passage of the third period of time the pump 235 is again turned OFF until the next scheduled reading cycle. Other specific schemes may be implemented to enable water to enter and exit the sampling chamber at the proper time. For example, water may be pumped into the chamber rather than allowed to enter by means of hydrostatic pressure as is shown in the illustrated example. Also, water level detectors may be implemented, for example, to determine when the sampling chamber is filled and/or emptied so as to close the valve and turn OFF the pump instead of controlling the valve and pump operations using predetermined time periods. Further, the initialization and time references for the filling, holding and evacuating of the sampling chamber may be taken directly from the clock on-board the circuit board 211 of the water sensing device 201 rather than synchronizing a clock on the circuit board of the sampling module 221 as is shown in the present example. In any implementation however, the present invention will be practiced by providing a sampling chamber containing water reading probes for a water sensing device and then controlling the flow of sampled water into and out of the chamber such that the probes are exposed to the water for only limited periods of time while readings are being taken by the probes.

Figure 3:
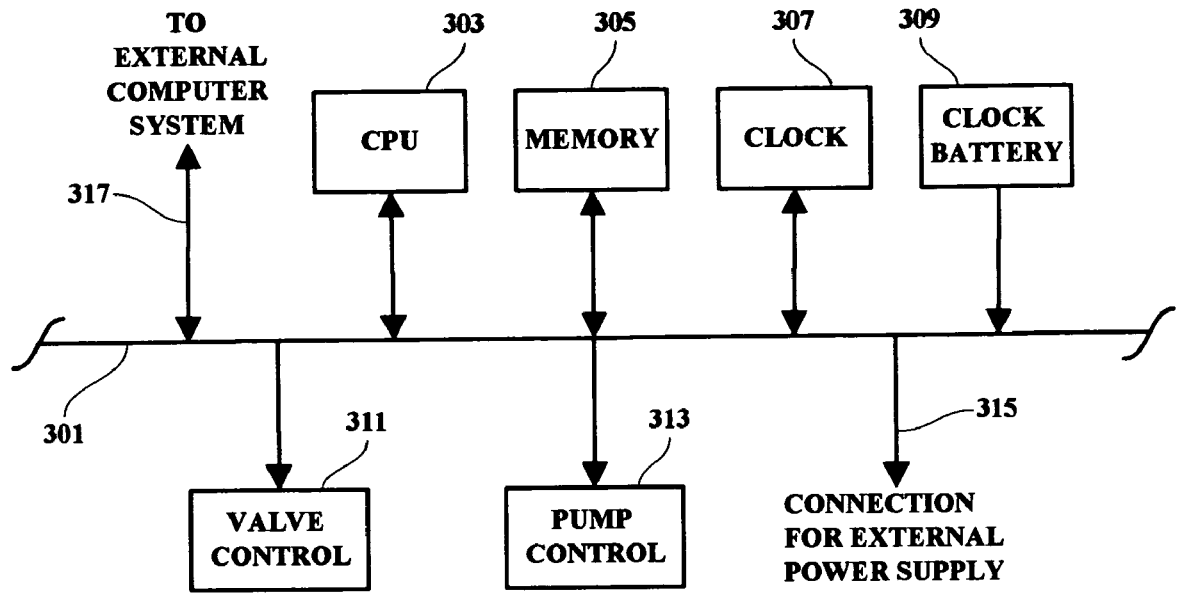
FIG. 3 is a schematic block diagram of the major electronic components of a circuit board utilized in an exemplary operation of the water sampling chamber portion of the water sensing system.

FIG. 3 is a schematic diagram of the major components of an exemplary circuit board 231 within the sampling module 221. As shown, the board contains a main interconnection bus 301 arranged to connect the various components of the board together. The bus 301 is connected to a CPU 303 or other main controller, and a memory device 305 which may comprise, for example, a flash memory unit. The memory 305 may be used to store operational programming for controlling the operation and timing of the sampling module 221. Also, connected to the bus 301 is a local clock 307, and a clock battery 309. In the present example, the on-board clock battery 309 is used to power only the clock and power for the other components on the board is provided from an external power supply through connector 315. The board also contains valve control and pump control components for controlling water input to the sampling chamber 231 through the valve 233 and water being evacuated from the sampling chamber 231 by the pump 235. The board also has a connector 317 for connecting the sampling module circuit board 231 to an external computer system, which may be a PC or laptop computer, for uploading and downloading information and also for testing purposes.

Figure 4:
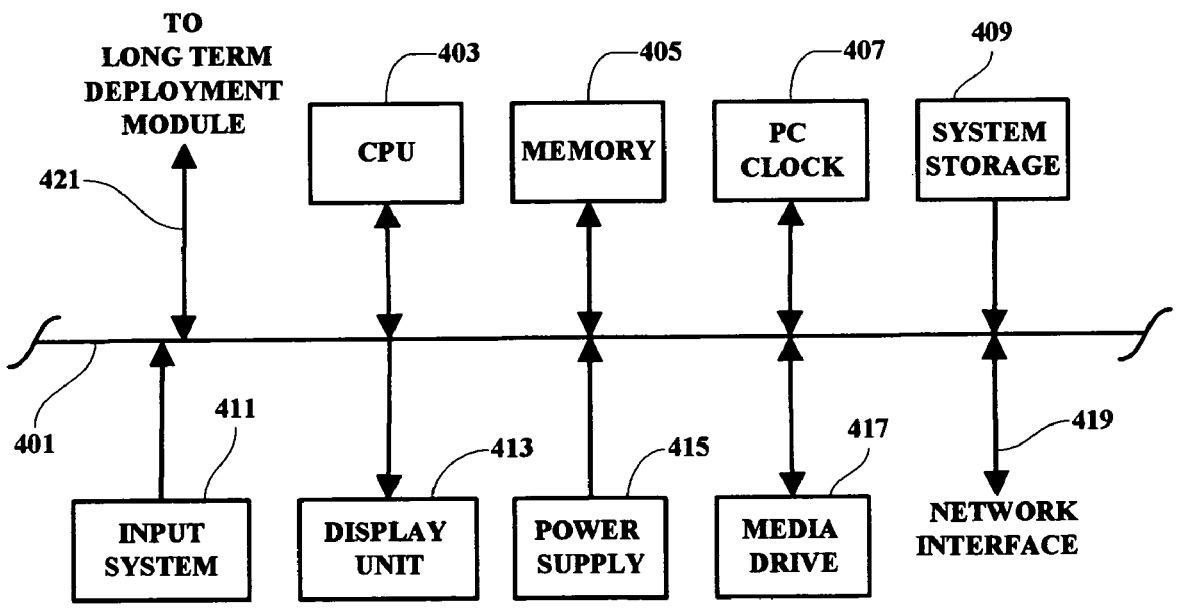
FIG. 4 is a schematic block diagram of the major electronic components of a personal computer which may be interfaced with the water sampling chamber portion of the illustrated sensing device.

FIG. 4 is a schematic diagram showing the major components of a computer system, e.g. a PC, to which the sampling module circuit board 231 or the sensing device circuit board 111 may be connected. As shown, the computer system includes a main interconnection bus 401 arranged to connect the various components of the system together. The bus is connected to a CPU 403, a memory unit 405, a PC clock 407, a storage system 409, an input system 411, a display unit 413, a power supply 415 a media drive 417 (such as a CD drive) and a network interface 419 for providing a connection to a network of computers which may be implemented in a larger water monitoring system. The PC also includes a connector 421 to the sensing device 101 and also to the sampling module 221. As hereinbefore discussed, where the electronics of the sampling module 221 and the sensing device 101 are integrated together, only one electrical connection, e.g. 421, will be required, although as illustrated in the present example, separate electrical cables are used, one each for the sensing device 101 and the sampling module 221. Other devices and components may also be connected to the main bus 401 depending upon particular applications.

Figure 5:
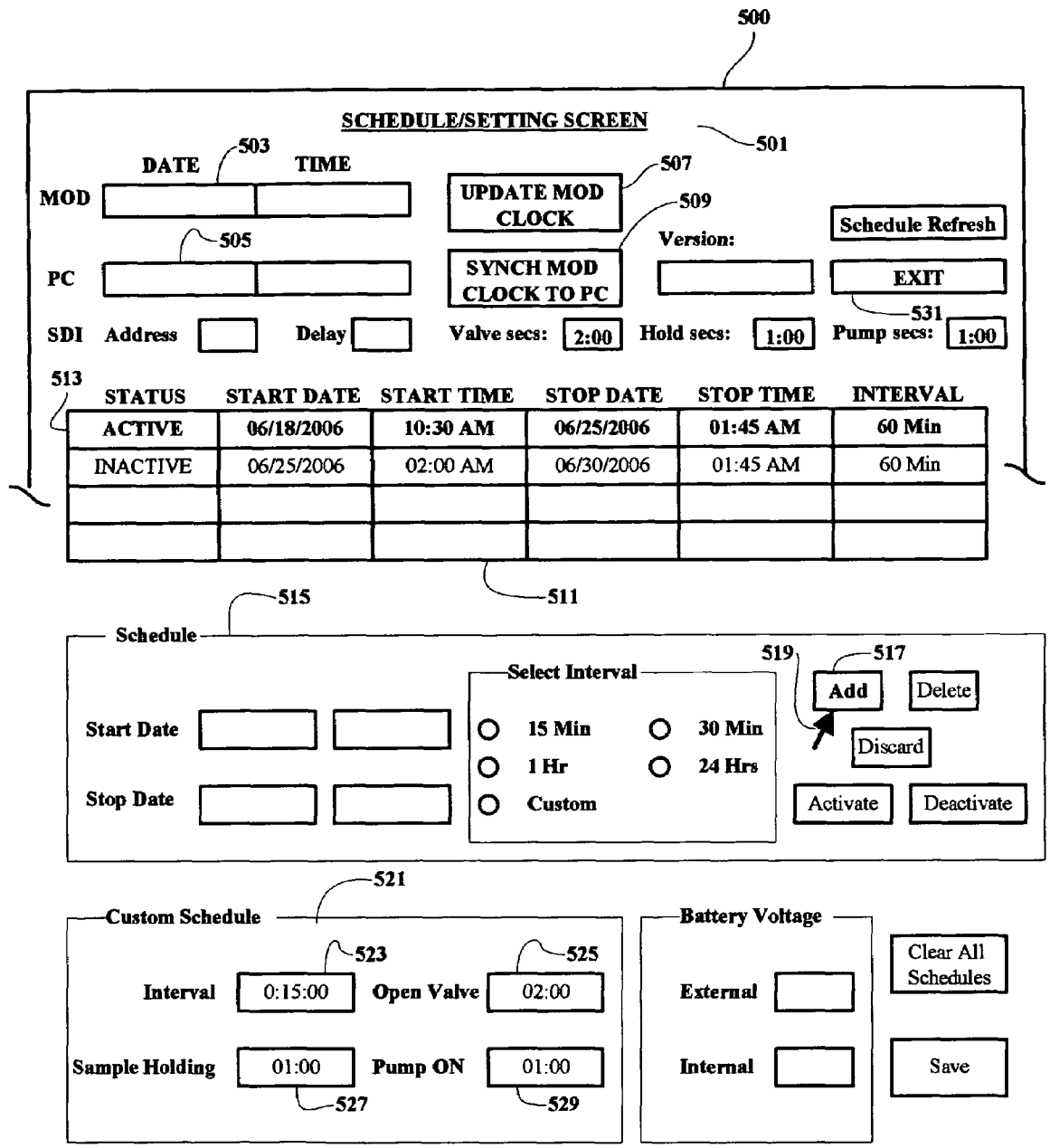
FIG. 5 is an illustration of an exemplary graphical user interface which may be used in connection with the present invention.

FIG. 5 illustrates an exemplary graphical user interface (GUI) 500 which may be used to schedule operations of the sampling module 221. As shown, a schedule and setting screen is presented on a display of the PC connected to the sampling module circuit board connector 317. The date and time 503 as contained in the memory of the sampling module 221 is displayed as well as the date and time 505 as contained in the clock system of the connected PC. By "pointing-and-clicking" a mouse-controlled pointer (e.g. 519) on the button 507 on the display screen or GUI 500, a user is enabled to update the module clock 307 to a designated reference which may be the clock on-board the sensing device 101/201. Another button 509 enables the user to synchronize the module clock 307 to the PC clock 407. In the example, the PC clock is also used to synchronize to the sensing device clock so that both the sensing device clock (not shown) and the sampling module clock 307 are in synchronization. This synchronization is an important step since the sensing device will be programmed to take readings at predetermined times and the operation of the sampling module must be coordinated such that when readings are taken by the probes 205-209, the sampling chamber 222 is filled with water, and the water is promptly evacuated from the sampling chamber after such readings have been completed. For example, the probes are generally programmed to take a measurement or reading every 15 minutes, 30 minutes or 60 minutes. The probes have to be powered-up for 2 minutes before taking a measurement or reading. When not taking measurements, the probes are dormant and are not powered-up in order to conserve power. If it takes, for example, 2 minutes to fill the sampling chamber with water, then the filling process i.e. the opening of valve 233 will need to begin prior to the time the probes are beginning to power-up in order to allow time for the water in the sampling chamber 222 to settle prior to taking measurements by the probes 205-209. Further, the pumping-out of the water from the sampling chamber 222 cannot begin until after the probes 205-209 have completed taking measurements. Thus, it is apparent that the operation of the sampling module 221 and the operation of the sensing device probes must be coordinated and synchronized.

The GUI 500 also includes a scheduling table 511 for displaying active and inactive schedules for the operation of the sampling module 221. An active-schedule 513 is one which has been activated and represents a current operating schedule for the sampling module and an inactive schedule is one which is not currently active. A schedule includes indications for the date and time for when the schedule is started and also the date and time for when the schedule is stopped as well as the interval or time between sampling operations. In a scheduling portion 515 of the GUI 500, a user is enabled to create a schedule by indicating start and stop dates and sampling interval. After inputting values for these selections, a user is enabled to ADD the schedule to the table 511 by pointing-and-clicking 519 on an ADD button 517. If a user selects "Custom" from the Select Interval section, the user is enabled to designate a Custom Schedule 521 including custom times for the sampling chamber operation. In the illustrated example, an Interval time period of 15 minutes 523, an Open Valve time period of 2 minutes 525, a Sample Holding time period of 1 minute 527 and a Pump ON time period of 1 minute are shown. These may also represent default time periods when specific time periods are not input. The GUI 500 also indicates the Battery Voltage. Other buttons enable a user to Clear All Schedules and to Save the input information and scheduling to the memory unit 305 of the sampling module 221. The GUI may be exited by pointing-and-clicking on the EXIT button 531.

At the designated intervals, for the time periods designated above for example, each sampling module operation consists of opening the valve 233 for 2 minutes, closing the valve and holding the sampling chamber closed for a period of 1 minute while the probes take measurements (typically in the middle of this 1 minute period), and then pumping 235-the sampling chamber water out of the chamber through the sample discharge line 251 for a time period of 1 minute. After pumping-out the sampling chamber, the probes are maintained at a "just moist" environment to keep the probes hydrated during the down time between measurements. The amount of water remaining in the sampling chamber 222 between measurements may vary depending, inter alia, on the pump-out time period, so long as the sampling chamber is substantially evacuated and the probes are not immersed in water when measurements are not being taken.

Figure 6:
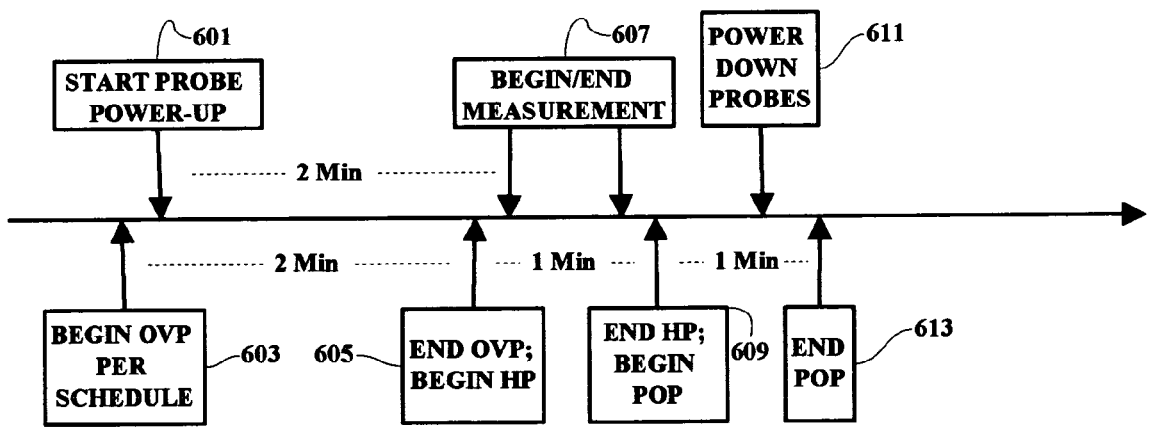
FIG. 6 is a timing chart illustrating the relative timing between various functions operating in a water sampling cycle.

As shown in FIG. 6, when it is time to begin a probe measurement cycle, the probes begin to be powered-up 601. In the example, this process takes 2 minutes. Since before measurements can be taken by the probes, the sampling chamber must be filled, the Open Valve Period (OVP) is initiated 603 prior to the time the probes are beginning to be powered-up. According to the scheduled cycle, the OVP period lasts for 2 minutes and is completed 605 prior to a time when the measurements are taken by the probes 607. When the OVP is completed, the holding period (HP) is initiated 605 during which time the valve 233 is closed and water is held in the sampling chamber 222 while the probe measurements are taken 607. The holding period begins 605 prior to the time the measurements are taken and ends 609 after the measurements are taken by the probes 607. After measurements are taken, the probes are powered down 611 to await the next sampling cycle and the holding period ends 609 while the Pump ON period begins and turns ON the pump to empty the sampling chamber 222. After 1 minute, the Pump ON period ends 613, the sampling chamber has been emptied and the pump 235 is turned OFF.

Figure 7:
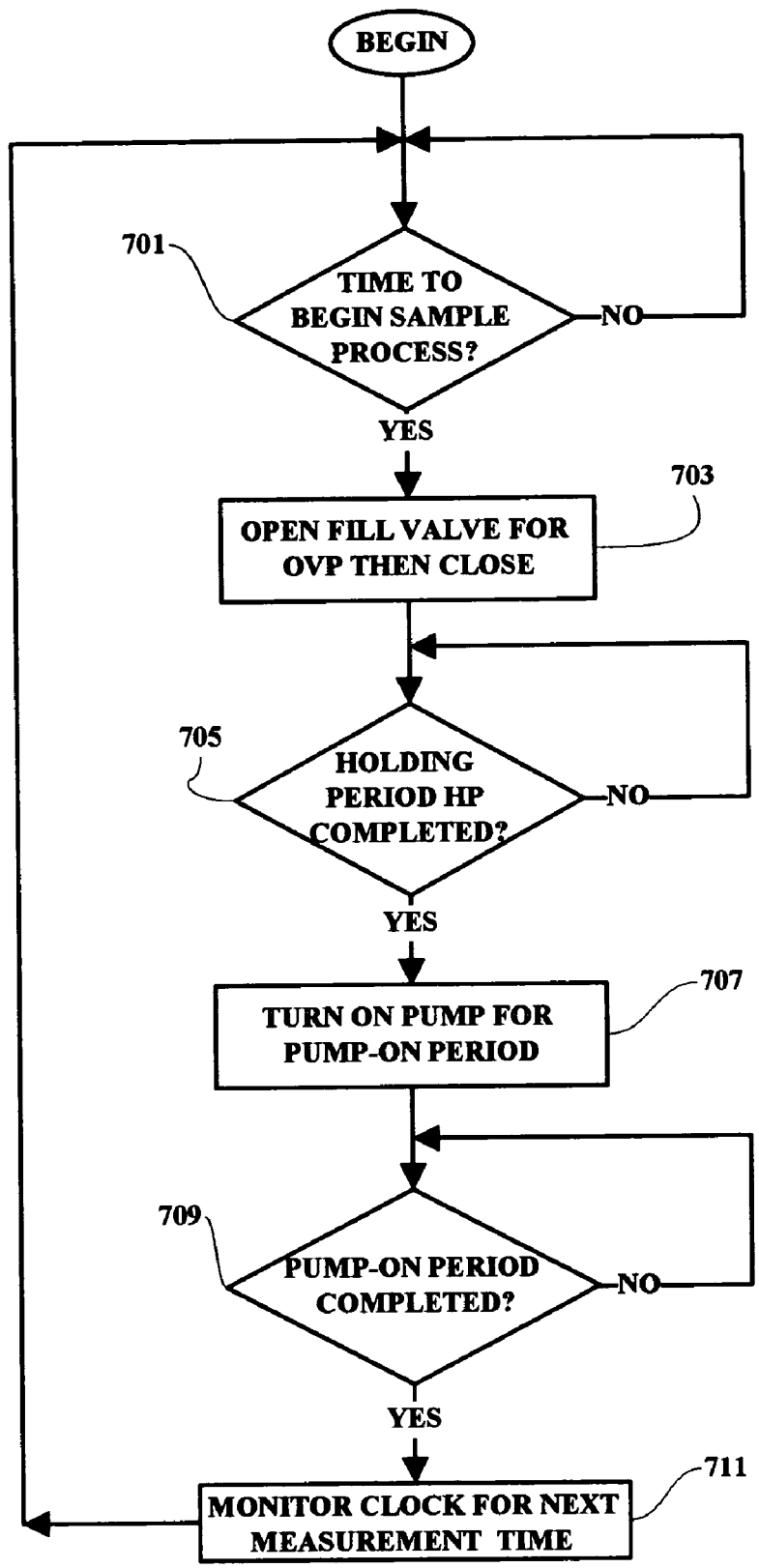
FIG. 7 is a flow chart illustrating an exemplary sequence of operations in a cyclic operation of the water sampling chamber portion of the illustrated sensing device.

FIG. 7 is a flow chart showing an exemplary sequence of operation for the sampling module 221. The process begins when it is determined by reference to the schedule GUI input 500 and module clock 307, that it is time to begin a sample process 701. The normally closed fill valve 233 is then opened 703 for the pre-set Open Valve period OVP and the valve is then allowed to close. After the Open Valve period has been completed, the Holding Period timing begins and lasts for a pre-set period of 1 minute for example. When it is determined that the Holding Period has been completed 705 and measurements have been taken by the probes 205-209, then the pump 235 is turned ON for the Pump ON Period 707 after which the pump is no longer powered ON and the processing returns to monitor the clock 307 and schedule 513 for the next scheduled sampling time 711. This processing may be implemented in software programming stored in the memory unit 305 of the sampling module 221 or in firmware or hardware and implemented on the circuit board 231 of the sampling module 221.

The method and apparatus of the present invention has been described in connection with a preferred embodiment as disclosed herein. The disclosed methodology may be implemented in many different specific embodiments to accomplish the desired results as herein illustrated. Although an embodiment of the present invention has been shown and described in detail herein, along with certain variants thereof, many other varied embodiments that incorporate the teachings of the invention may be easily constructed by those skilled in the art. Portions of the disclosed methodology may also be implemented solely or partially in program code stored on a CD, disk or diskette (portable or fixed), or other memory device, from which it may be loaded into memory and executed to achieve the beneficial results as described herein. Accordingly, the present invention is not intended to be limited to the specific form set forth herein, but on the contrary, it is intended to cover such alternatives, modifications, and equivalents, as can be reasonably included within the spirit and scope of the invention.

What is claimed is:

1. A method for using water measuring probes of a water sensing device to measure predetermined characteristics of water proximate to said probes, said method comprising:
   providing a water-sealed sampling chamber enclosing said probes from water proximate to said water sensing device, said sampling chamber being constructed to be submerged in a body of water of which said predetermined characteristics are to be measured;
   providing an air passage device from said sampling chamber to outside air at ambient atmospheric pressure above said body of water to enable drawing a flow of outside air into said sampling chamber to replace water being pumped out of said sampling chamber; and
   controlling a flow of water into and out of said sampling chamber when said sampling chamber is submerged in said body of water whereby water from said body of water is in contact with said probes only during a predetermined measuring time period when said probes are measuring said predetermined characteristics of water in said sampling chamber.

2. The method as set forth an claim 1 wherein said air passage device is a tube connecting an upper portion of said sampling chamber to outside air above said body of water.

3. The method as set forth in claim 2 wherein said water flow into said sampling chamber is controlled by operating a valve device.

4. The method as set forth in claim 3 wherein said valve device is normally closed and selectively opened to allow water into said sampling chamber at predetermined times for said measuring.

5. The method as set forth in claim 4 and further including selectively evacuating water from said sampling chamber after said probes have completed measuring said predetermined characteristics of water in said sampling chamber while maintaining said sampling chamber submerged in said body of water.

6. The method as set forth in claim 5 wherein said sampling chamber is evacuated using a selectively operable pump device.

7. The method as set forth in claim 1 and further including selectively evacuating water from said sampling chamber after said probes have completed measuring said predetermined characteristics of water in said sampling chamber while maintaining said sampling chamber submerged in said body of water.

8. The method as set forth in claim 7 wherein said sampling chamber is evacuated using a selectively operable pump device.

9. A computer-readable memory medium within a control system, said computer-readable memory medium containing program code to control presence of water in a water-sealed sampling chamber of an associated water sensing device, said water sensing device including one or more water measuring probes enclosed within said sampling chamber, said sampling chamber being constructed to be submerged in a body of water of which said predetermined characteristics are to be measured, said sampling chamber being coupled to outside air at ambient atmospheric pressure above said body of water by an air passage device to enable drawing a flow of outside air into said sampling chamber to replace water being pumped out of said sampling chamber, said probes being selectively operable for measuring predetermined characteristics of water in said sampling chamber at predetermined times, said computer-readable memory medium being programmed to selectively generate program signals, said program signals being readable by said control system for controlling a flow of water into and out of said sampling chamber when said sampling chamber is submerged in said body of water whereby water from said body of water is in contact with said probes only during a predetermined measuring time period when said probes are measuring said predetermined characteristics of water in said sampling chamber.

10. The computer-readable memory medium as set forth in claim 9 wherein said computer-readable memory medium is a memory unit coupled to control circuitry on a circuit board, said control circuitry being selectively operable for accessing said memory unit in controlling operations of said water input device and said water output device.

11. The computer-readable memory medium as set forth in claim 9 wherein said water sensing device further includes means for selectively connecting said water sensing device to an external computer system, said computer system being selectively operable for providing a graphical user interface (GUI) on a display device of said computer system, said GUI being operable for enabling a user to input selected values related to said controlling of said water input device and said water output device.

12. The computer-readable memory medium as set forth in claim 11 wherein said selected values include a time period during which water is allowed to enter said sampling chamber.

13. The computer-readable memory medium as set forth in claim 11 wherein said selected values include a time period during which water is held within said sampling chamber.

14. The computer-readable memory medium as set forth in claim 11 wherein said selected values include a time period during which water is evacuated from said sampling chamber.

15. The computer-readable memory medium as set forth in claim 11 wherein said GUI further includes means for selectively synchronizing operations of said water input device and said water output device with operations of said water measuring probes.

16. An attachment for use with a water sensing device, said water sensing device including measuring probes for measuring predetermined characteristics of water proximate to said water sensing device when said water sensing device is immersed in a body of water, said attachment comprising:
   a sampling chamber arranged to be attached to said water sensing device to enclose said measuring probes of said water sensing device in a water-tight configuration, said sampling chamber being constructed to be submerged in a body of water of which said predetermined characteristics are to be measured, said sampling chamber including means arranged for connection to an air passage device from said sampling chamber to outside air at ambient atmospheric pressure above said body of water to enable drawing a flow of outside air into said sampling chamber to replace water being pumped out of said sampling chamber; and control means for controlling a flow of water into and out of said sampling chamber when said sampling chamber is submerged in said body of water whereby water from said body of water is in contact with said probes only during a predetermined measuring time period when said probes are measuring said predetermined characteristics of water in said sampling chamber.

17. The attachment of claim 16 wherein said control means further includes;

a water input device for selectively controlling water flow into said sampling chamber;

a water output device for selectively controlling water flow out of said sampling chamber; and an electronically programmable control means for selectively operating said water input device and said water output device.

18. The attachment as set forth in claim 17 wherein said electronically programmable control means further includes memory means, said memory means containing input data accessed by said control means for controlling times of operation of said water input device and said water output device.

19. The attachment as set forth in claim 18 and further including electrical connection means arranged to provide an electrical connection to an external computer system, said external computer system including means for displaying a graphical user interface (GUI), said GUI further including means for enabling a user to input times of operation of said water input device and said water output device.

20. A water sample measuring apparatus comprising:

a water sensing device, said water sensing device including measuring probes for measuring predetermined characteristics of a water sample when said water sample measuring apparatus is immersed in a body of water;

a sampling chamber enclosing said measuring probes, said sampling chamber being constructed to be submerged in a body of water of which said predetermined characteristics are to be measured, said sampling chamber being water sealed from said body of water to prevent water from entering said sampling chamber;

means arranged for connection to an air passage device connecting said sampling chamber to outside air at ambient atmospheric pressure above said body of water to enable drawing a flow of outside air into said sampling chamber to replace water being pumped out of said sampling chamber; and means for controlling a flow of water into and out of said sampling chamber when said sampling chamber is submerged in said body of water whereby water from said body of water is in contact with said measuring probes only during a predetermined measuring time period when said measuring probes are measuring said predetermined characteristics of water in said sampling chamber.

\* \* \* \* \*